US011338071B2

(12) United States Patent
Jardret et al.

(10) Patent No.: US 11,338,071 B2
(45) Date of Patent: May 24, 2022

(54) FLUID WASTE CANISTER

(71) Applicant: DeRoyal Industries, Inc., Powell, TN (US)

(72) Inventors: Vincent Denis Jardret, Powell, TN (US); Walter Cleveland Cowart, Blaine, TN (US); Ethan Edward Valentine, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 66 days.

(21) Appl. No.: 16/418,448

(22) Filed: May 21, 2019

(65) Prior Publication Data
US 2019/0365960 A1 Dec. 5, 2019

Related U.S. Application Data

(60) Provisional application No. 62/678,005, filed on May 30, 2018.

(51) Int. Cl.
*A61M 1/00* (2006.01)

(52) U.S. Cl.
CPC ....... *A61M 1/0001* (2013.01); *A61M 2202/08* (2013.01)

(58) Field of Classification Search
CPC .. B65D 1/0261; B65D 1/0276; B65D 1/0284; A61M 1/0001
See application file for complete search history.

(56) References Cited

U.S. PATENT DOCUMENTS

| | | | | |
|---|---|---|---|---|
| 3,926,324 A | * | 12/1975 | Zavasnik | B29C 49/06 215/373 |
| 4,261,473 A | * | 4/1981 | Yamada | B29C 49/0005 215/379 |
| 4,380,306 A | * | 4/1983 | Knopf | B65D 1/12 220/606 |
| 5,066,081 A | * | 11/1991 | Bartley | B29C 49/0073 215/373 |
| 5,256,160 A | * | 10/1993 | Clement | B01J 37/10 604/319 |
| 5,772,126 A | | 6/1998 | Hanvey, Jr. et al. | |
| 6,269,964 B1 | * | 8/2001 | Turner, Jr. | A47J 36/027 206/564 |
| 2007/0084822 A1 | * | 4/2007 | Bohen | B65D 11/04 215/382 |
| 2008/0015526 A1 | | 1/2008 | Reiner et al. | |
| 2011/0139667 A1 | | 6/2011 | Burgess et al. | |

* cited by examiner

*Primary Examiner* — Andrew T Kirsch
(74) *Attorney, Agent, or Firm* — Luedeka Neely Group, PC

(57) ABSTRACT

A fluid medical waste canister has interior surfaces that are exposed only to compressive stresses when a vacuum is applied, thereby eliminating the potential for environmental stress cracking. The canister is compatible with medical procedures that generate fluids having high fat/lipid content, such as liposuction procedures. The canister avoids certain stress concentration distributions that cause cracks to close onto themselves, which can cause one or more pieces of the canister wall to rupture into its interior volume. Because the canister is designed to avoid conditions that initiate canister implosion during liposuction procedures, low-cost polystyrene may be used as a waste canister material for such procedures.

22 Claims, 5 Drawing Sheets

(Section A-A)

(Section A-A)

(Detail B)

(Detail C)

(Section A-A)

(Detail B)

(Detail C)

(Section A-A)

(Detail B)

(Detail C)

(Section A-A)

(Detail B)

(Detail C)

(Section A-A)

(Detail B)

(Detail C)

FLUID WASTE CANISTER

RELATED APPLICATIONS

This application claims priority to provisional patent application Ser. No. 62/678,005 titled "Waste Fluid Management Canister with Improved Molecular Synergy When Under Vacuum" filed May 30, 2018.

FIELD

This invention relates to the field of medical fluid waste management. More particularly, this invention relates to a fluid waste management canister having improved molecular synergy when exposed to a vacuum.

BACKGROUND

Waste management canisters used in medical applications are usually made of polystyrene. They are known to be susceptible to failure when used in medical procedures that generate fluids with high concentrations of fats (lipids). Because of the risk of failure, such canisters must not be used for procedures that will generate such conditions. This failure mode is caused by a phenomenon known as environmental stress cracking, which may be caused by a number of initiators, including chemicals and ionizing radiations. However, for environmental stress cracking to occur, the effect of the initiator must be combined with tensile stresses in the material.

A common solution to the problem of environmental stress cracking is to use a canister material that is more resistant to the initiators than is polystyrene. However, this can be cost prohibitive for the intended use of these canisters.

Most conventional canisters used for fluid waste management have several different locations at which their internal surfaces are subject to tensile stresses when exposed to vacuum. Under these conditions, environmental stress cracking can occur when these surfaces are exposed to potential initiators in the fluids they contain. Accordingly, such canisters are contraindicated for use with liposuction or other high lipid content procedures. Up to now, there has been no attempt to change the shape of the canister—without changing the canister material—to address this problem.

What is needed, therefore, is a waste management canister constructed from a low-cost material having a shape that is not susceptible to environmental stress cracking when exposed to initiators, such as fluids with high concentrations of lipids.

SUMMARY

The above and other needs are met by a canister having interior surfaces that are exposed only to compressive stresses when a vacuum is applied, thereby eliminating the potential for environmental stress cracking. A canister designed with such features is compatible with medical procedures that generate fluids having high fat/lipid content, such as liposuction procedures.

Embodiments described herein avoid certain stress concentration distributions that cause cracks to close onto themselves, which could cause one or more pieces of the canister wall to rupture into the interior volume of the canister. Such an implosion could result in the spread of the canister contents around a surgical suite or hospital room. Since preferred embodiments described herein avoid conditions that initiate canister implosion during liposuction procedures, these embodiments enable the use of low-cost polystyrene as a waste canister material for such procedures.

Some preferred embodiments described herein are directed to a medical fluid waste canister comprising a reservoir. The reservoir includes a sidewall, a circular open top portion disposed at the top of the sidewall, a domed bottom portion disposed at the bottom of the sidewall, a smooth transition from the domed bottom portion to the bottom of the sidewall, and an interior surface that contains only concave areas over at least the bottom half of the height of the reservoir. In some embodiments, the sidewall is cylindrical or conical.

In some embodiments, the domed bottom portion has an elliptically shaped cross-section or a spherically shaped cross-section.

In some embodiments, the canister further comprises a support structure attached to the domed bottom portion of the reservoir for maintaining the canister in an upright position on a flat surface.

In some embodiments, the support structure comprises an annular rim, wedges, ridges, rib feet, or elliptically shaped feet.

In some embodiments, the support structure comprises an annular rim having a diameter that is smaller than the diameter of the reservoir at the smooth transition.

In some embodiments, the support structure comprises an annular rim that forms an extension of the sidewall and has a diameter substantially equivalent to the diameter of the reservoir at the smooth transition.

In some embodiments, the reservoir and the support structure are integrally formed from a continuous piece of material.

In some embodiments, the sidewall of the reservoir has a thickness ranging from about 0.05 inch to about 0.125 inch.

In some embodiments, the ratio of the thickness of the sidewall to the diameter of the sidewall ranges from 0.001 to 0.25.

In some embodiments, the reservoir is formed from polystyrene or or polymethyl methacrylate.

In some embodiments, the circular open top portion of the reservoir is configured to receive a lid.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1A:
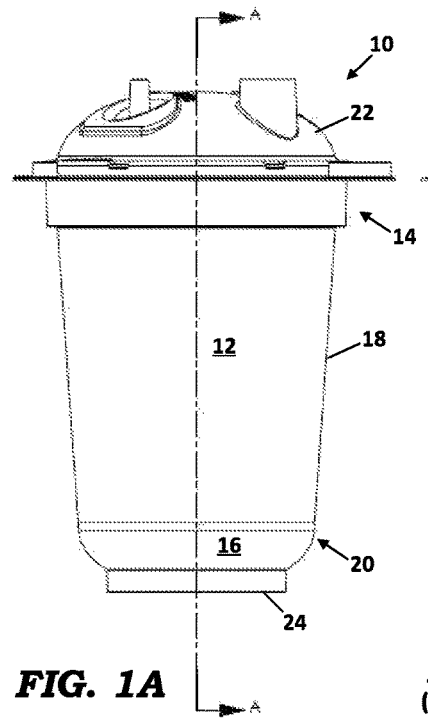
FIG. 1A depicts an elevation view of a fluid medical waste canister according to a first embodiment of the invention.
Figure 1B:
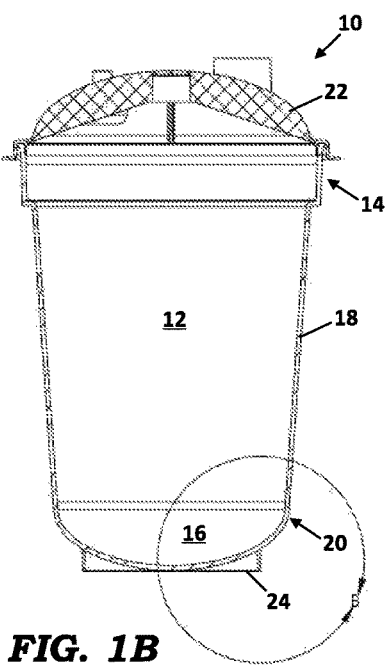
FIG. 1B depicts a cross-section view of the fluid medical waste canister according to the first embodiment.
Figure 1C:
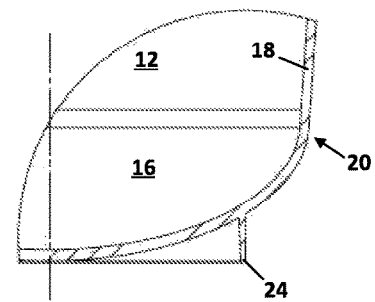
FIG. 1C depicts a detail cross-section view of the fluid medical waste canister according to the first embodiment.
Figure 1D:
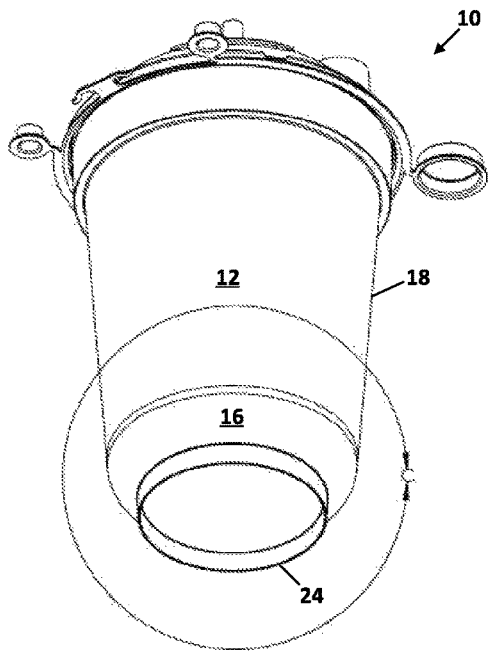
FIG. 1D depicts a bottom perspective view of the fluid medical waste canister according to the first embodiment.
Figure 1E:
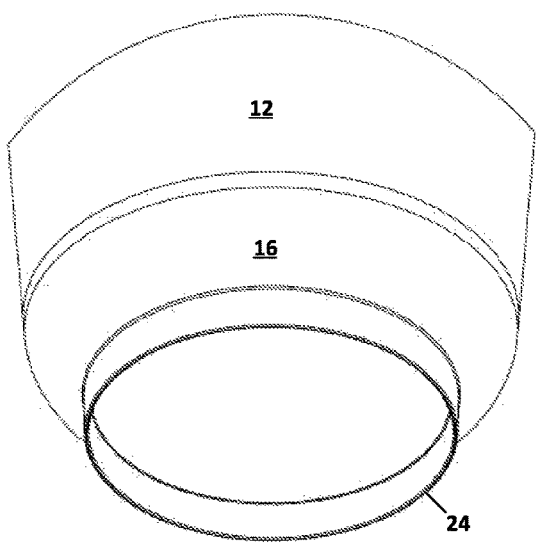
FIG. 1E depicts a bottom detail perspective view of the fluid medical waste canister according to the first embodiment.

According to a first embodiment as depicted in FIGS. 1A-1E, a medical fluid waste canister 10 includes a reservoir 12 having a sidewall 18, a dome-shaped bottom portion 16, and circular open top portion 14 that receives a lid 22. There is preferably a smooth transition 20 from the sidewall 18 to the bottom portion 16. As the term is used herein, a "smooth transition" refers to a region having no discontinuous surface features that would tend to introduce stress cracks upon exposure to compressive stresses. Below the smooth transition 20, the vertical cross-section of the bottom portion 16 is preferably elliptical in shape, although other shapes could be implemented, such as spherical, dished, or convex. Above the smooth transition 20, the sidewall 18 is generally conical or cylindrical. The thickness of the sidewall 18 may range from about 0.05 inch to 0.125 inch. The ratio of sidewall thickness to canister diameter preferably ranges from 0.001 to 0.25. The reservoir 12 is preferably formed from Styrenic-based resins and blends including but not limited to ABS (Acrylonitrile Butadiene Styrene), Crystal PS (polystyrene), SAN (Styrene-acrylonitrile), and MABS (Methyl methacrylate Acrylonitrile Butadiene Styrene), although it could be formed from other materials, such as Acrylic-based resins and blends such as PMMA (polymethyl methacrylate) or polycarbonate. A support structure 24 is provided on the bottom portion 16 on which the canister 10 can stand upright. In the first embodiment, the support structure 24 is a ring-shaped rim. In other embodiments, the support structure 24 comprises wedges, ridges, or other types of protrusions provided on the bottom portion 16 to keep the canister 10 standing upright.

Figure 2A:
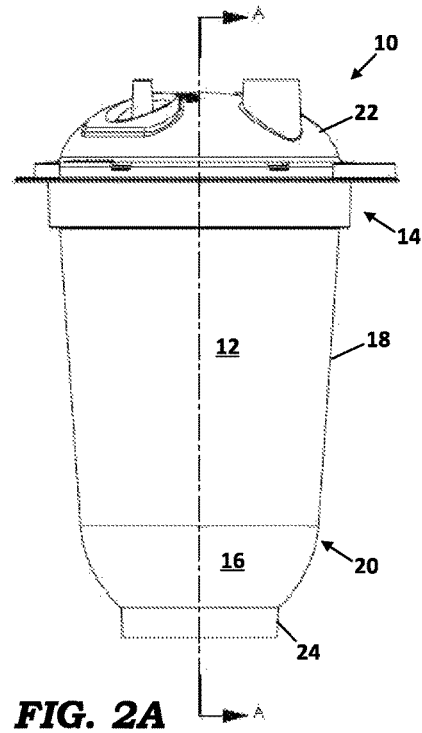
FIG. 2A depicts an elevation view of a fluid medical waste canister according to a second embodiment of the invention.
Figure 2B:
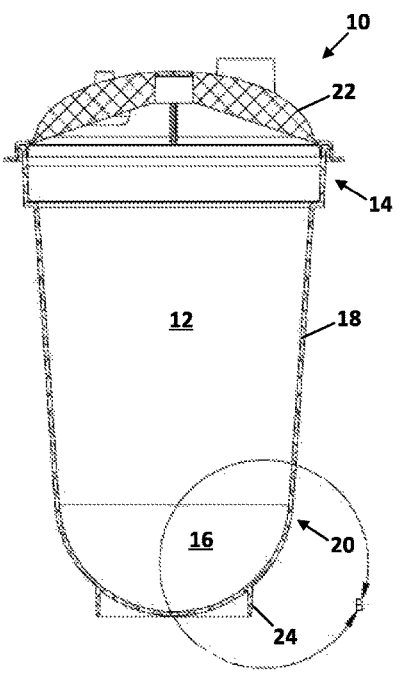
FIG. 2B depicts a cross-section view of the fluid medical waste canister according to the second embodiment.
Figure 2C:
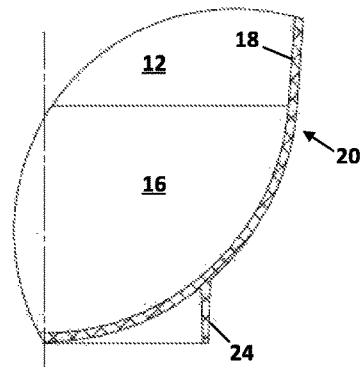
FIG. 2C depicts a detail cross-section view of the fluid medical waste canister according to the second embodiment.
Figure 2D:
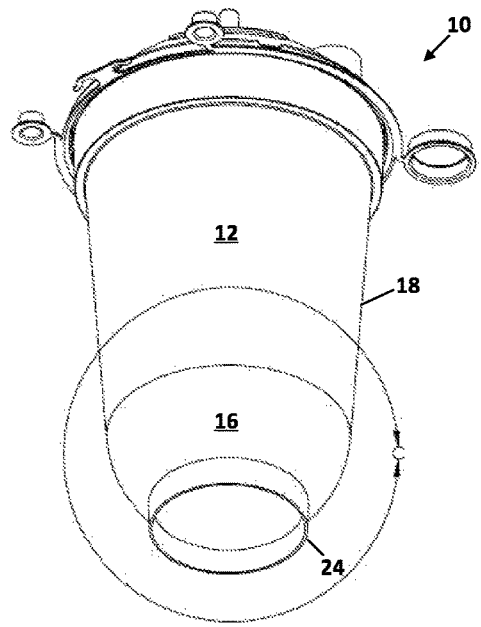
FIG. 2D depicts a bottom perspective view of the fluid medical waste canister according to the second embodiment.
Figure 2E:
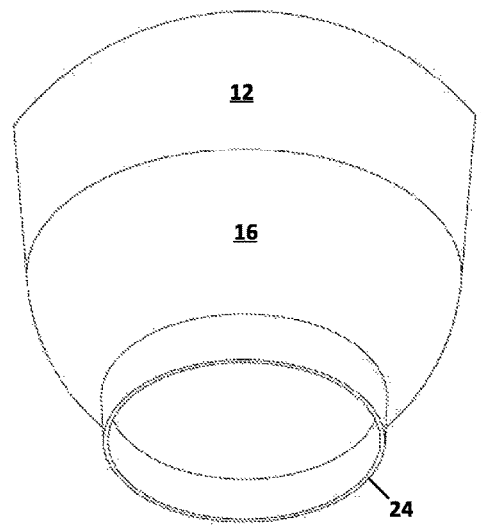
FIG. 2E depicts a bottom detail perspective view of the fluid medical waste canister according to the second embodiment.

A second embodiment depicted in FIGS. 2A-2E is generally similar to the first embodiment, except that the dome-shaped bottom portion 16 is spherical.

Figure 3A:
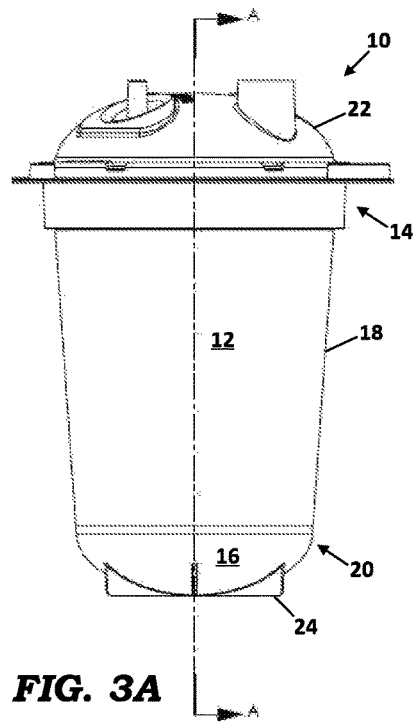
FIG. 3A depicts an elevation view of a fluid medical waste canister according to a third embodiment of the invention.
Figure 3B:
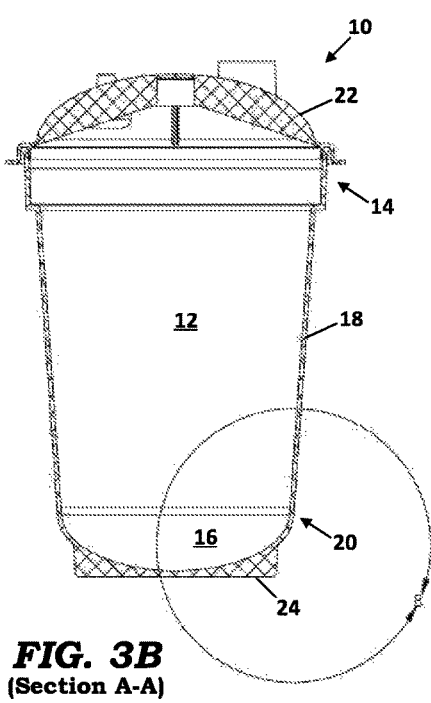
FIG. 3B depicts a cross-section view of the fluid medical waste canister according to the third embodiment.
Figure 3C:
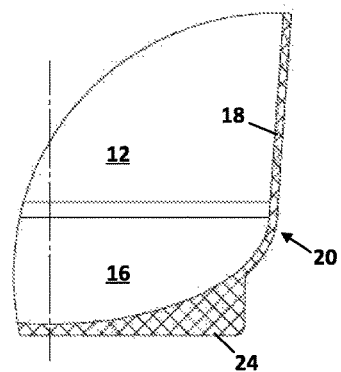
FIG. 3C depicts a detail cross-section view of the fluid medical waste canister according to the third embodiment.
Figure 3D:
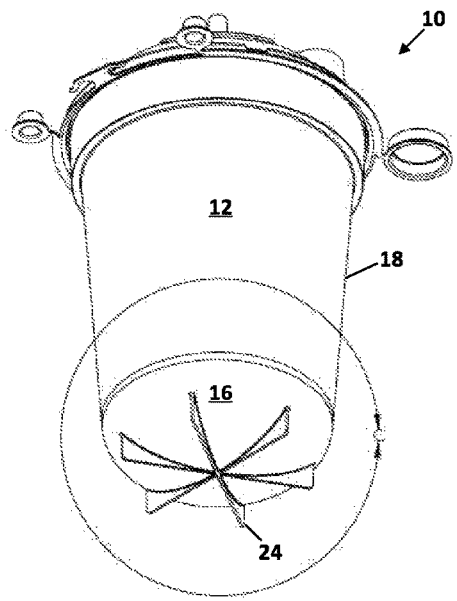
FIG. 3D depicts a bottom perspective view of the fluid medical waste canister according to the third embodiment.
Figure 3E:
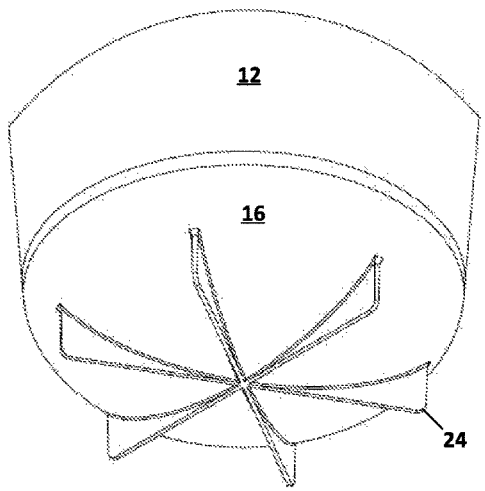
FIG. 3E depicts a bottom detail perspective view of the fluid medical waste canister according to the third embodiment.

A third embodiment depicted in FIGS. 3A-3E is generally similar to the first embodiment, except that the support structure 24 comprises a set of rib feet.

Figure 4A:
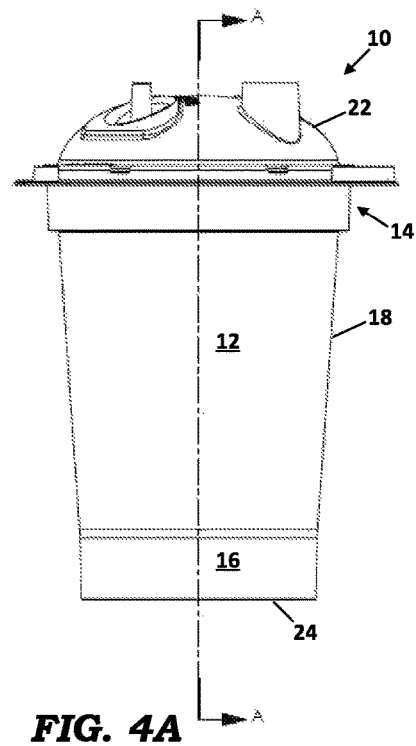
FIG. 4A depicts an elevation view of a fluid medical waste canister according to a fourth embodiment of the invention.
Figure 4B:
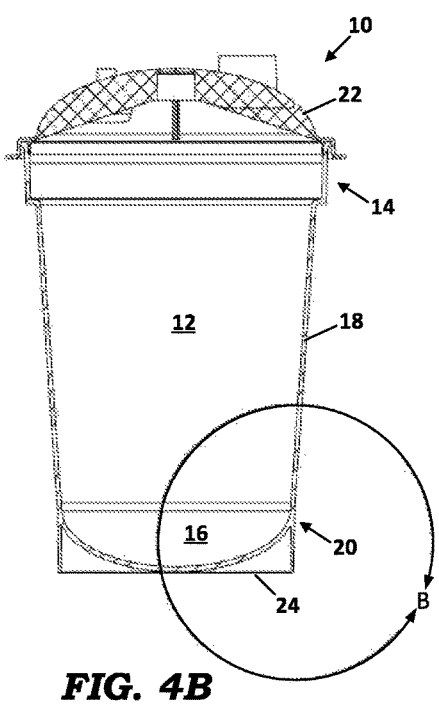
FIG. 4B depicts a cross-section view of the fluid medical waste canister according to the fourth embodiment.
Figure 4C:
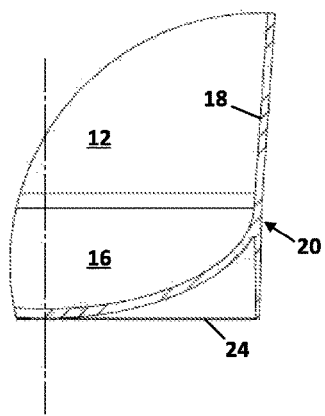
FIG. 4C depicts a detail cross-section view of the fluid medical waste canister according to the fourth embodiment.
Figure 4D:
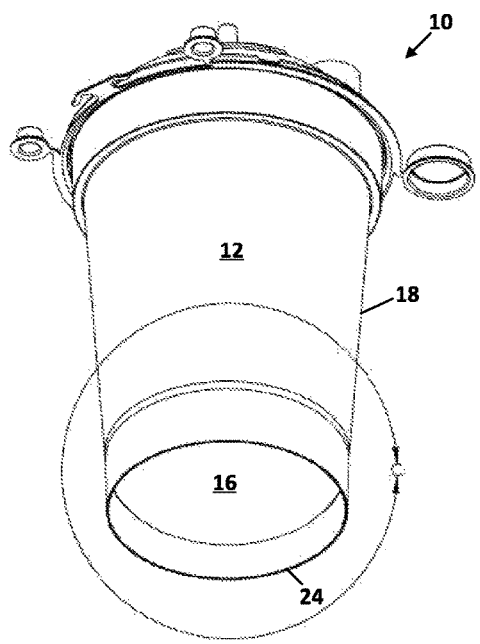
FIG. 4D depicts a bottom perspective view of the fluid medical waste canister according to the fourth embodiment.
Figure 4E:
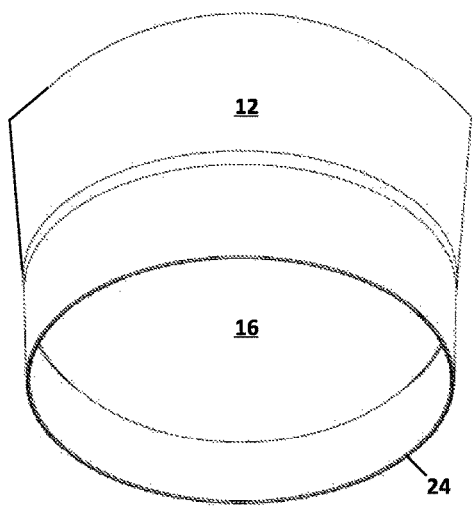
FIG. 4E depicts a bottom detail perspective view of the fluid medical waste canister according to the fourth embodiment.

A fourth embodiment depicted in FIGS. 4A-4E is generally similar to the first embodiment, except that the support structure 24 comprises a rim extending downward from near the smooth transition 20.

Figure 5A:
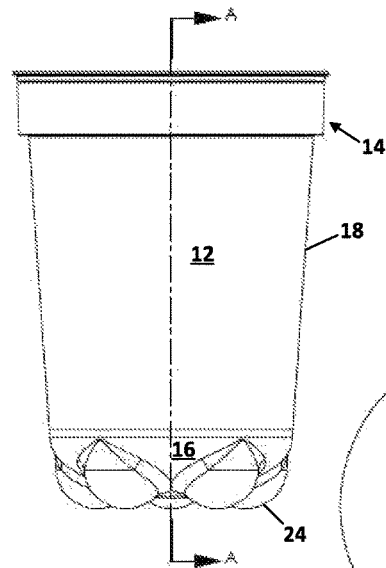
FIG. 5A depicts an elevation view of a fluid medical waste canister according to a fifth embodiment of the invention.
Figure 5B:
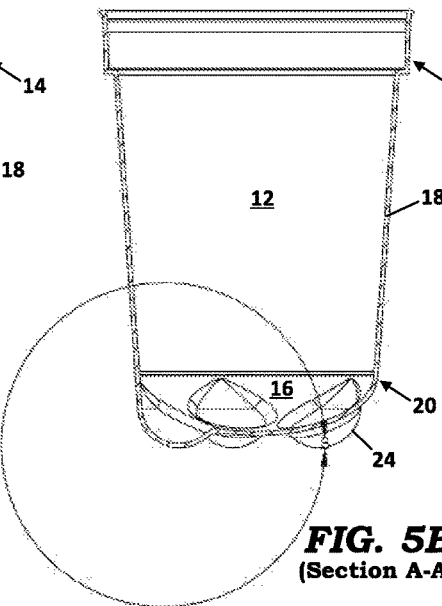
FIG. 5B depicts a cross-section view of the fluid medical waste canister according to the fifth embodiment.
Figure 5C:
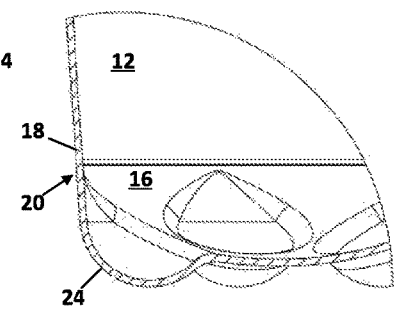
FIG. 5C depicts a detail cross-section view of the fluid medical waste canister according to the fifth embodiment.
Figure 5D:
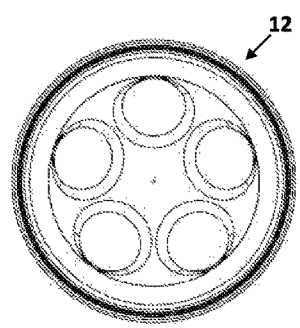
FIG. 5D depicts a bottom plan view of the fluid medical waste canister according to the fifth embodiment.
Figure 5E:
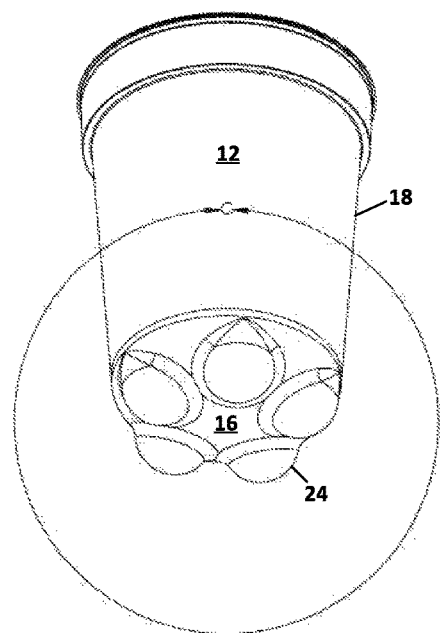
FIG. 5E depicts a bottom perspective view of the fluid medical waste canister according to the fifth embodiment.
Figure 5F:
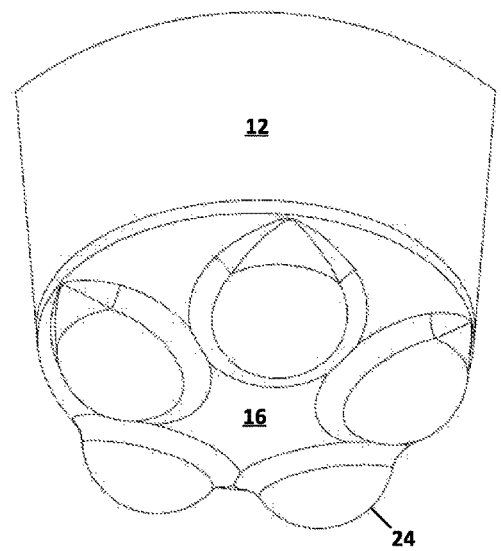
FIG. 5F depicts a bottom detail perspective view of the fluid medical waste canister according to the fifth embodiment.

A fifth embodiment depicted in FIGS. 5A-5F is generally similar to the first embodiment, except that the support structure 24 comprises a set of elliptically shaped feet that are distributed radially around the bottom portion 16. The fifth embodiment is an example of an alternative design that has some concave areas. Although such concave areas could lead to potential cracking, the shape of the surrounding areas provide structural reinforcement to the canister wall 18, such that cracks would not close onto themselves and lead to the formation of a loose piece of the wall that could implode inside the canister 10.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A medical fluid waste canister comprising:
   a circular lid; and
   a reservoir comprising:
   a sidewall having a bottom and a top;
   a domed bottom portion disposed at the bottom of the sidewall;
   a smooth transition from the domed bottom portion to the bottom of the sidewall, wherein the bottom of the sidewall has a first diameter at the smooth transition;
   a circular opening at the top of the sidewall at which the circular lid is received, the circular opening having a second diameter that is greater than or equal to the first diameter; and
   an interior surface of the reservoir that contains only concave areas over at least a bottom half of a height of the reservoir.

2. The medical fluid waste canister of claim 1 wherein the sidewall is cylindrical or conical.

3. The medical fluid waste canister of claim 1 wherein the domed bottom portion has an elliptically shaped cross-section.

4. The medical fluid waste canister of claim 1 wherein the domed bottom portion has a spherically shaped cross-section.

5. The medical fluid waste canister of claim 1 further comprising a support structure attached to the domed bottom portion of the reservoir for maintaining the canister in an upright position on a flat surface.

6. The medical fluid waste canister of claim 5 wherein the support structure comprises one or more of an annular rim, wedges, ridges, and rib feet.

7. The medical fluid waste canister of claim 5 wherein the support structure comprises an annular rim having a diameter that is smaller than a diameter of the reservoir at the smooth transition.

8. The medical fluid waste canister of claim 5 wherein the support structure comprises an annular rim that forms an extension of the sidewall and has a diameter substantially equivalent to the first diameter.

9. The medical fluid waste canister of claim 5 wherein the reservoir and the support structure are integrally formed from a continuous piece of material.

10. The medical fluid waste canister of claim 1 wherein the sidewall of the reservoir has a thickness ranging from about 0.05 inch to about 0.125 inch.

11. The medical fluid waste canister of claim 1 wherein a ratio of a thickness of the sidewall to a diameter of the sidewall ranges from 0.001 to 0.25.

12. The medical fluid waste canister of claim 1 wherein the reservoir is formed from one or more of polystyrene and polymethyl methacrylate.

13. A medical fluid waste canister having an interior surface defined by:
   a conical sidewall having a bottom and a top, wherein the bottom of the sidewall has a first diameter;
   a circular open top portion disposed at the top of the sidewall, the circular open top portion having a second diameter that is greater than the first diameter;
   a domed bottom portion disposed at the bottom of the sidewall; and
   a smooth transition from the domed bottom portion to the bottom of the sidewall,
wherein the interior surface of the canister is subject to only compressive stresses over a bottom half of the canister when a vacuum is created inside the canister.

14. The medical fluid waste canister of claim 13 wherein the domed bottom portion has an elliptically shaped cross-section or a spherically shaped cross-section.

15. The medical fluid waste canister of claim 13 wherein the sidewall has a thickness ranging from about 0.05 inch to about 0.125 inch.

16. The medical fluid waste canister of claim 13 wherein a ratio of a thickness of the sidewall to a diameter of the sidewall ranges from 0.001 to 0.25.

17. A medical fluid waste canister comprising:
   a reservoir comprising:
      a conical sidewall having a thickness ranging from about 0.05 inch to about 0.125 inch, the sidewall having a bottom and a top, wherein the bottom of the sidewall has a first diameter;
      a circular open top portion disposed at the top of the sidewall that is configured to receive a lid, the circular open top portion having a second diameter that is greater than the first diameter;
      a domed bottom portion disposed at the bottom of the sidewall, the domed bottom portion having an elliptically shaped cross-section or a spherically shaped cross-section; and
      a smooth transition from the domed bottom portion to the bottom of the sidewall,
      wherein an interior surface of the reservoir contains no convex areas over at least a bottom half of a height of the reservoir; and
   a support structure attached to the domed bottom portion of the reservoir for maintaining the canister in an upright position on a flat surface, the support structure comprising one or more of an annular rim, wedges, ridges, and rib feet.

18. The medical fluid waste canister of claim 17 wherein the reservoir and the support structure are integrally formed from a continuous piece of material.

19. A medical fluid waste canister comprising:
   a reservoir comprising:
      a sidewall having a bottom and a top, wherein the bottom of the sidewall has a first diameter;
      a circular open top portion disposed at the top of the sidewall, the circular open top portion having a second diameter that is greater than the first diameter;
      a domed bottom portion disposed at the bottom of the sidewall; and
      a smooth transition from the domed bottom portion to the bottom of the sidewall; and
   a support structure attached to the domed bottom portion of the reservoir for maintaining the canister in an upright position on a flat surface, the support structure comprising elliptically shaped feet.

20. The medical fluid waste canister of claim 19 wherein the elliptically shaped feet are radially distributed around the domed bottom portion.

21. The medical fluid waste canister of claim 19 wherein the reservoir and the elliptically shaped feet are integrally formed from a continuous piece of material.

22. A method for use of a medical fluid waste canister having an interior surface defined by a conical sidewall having a bottom and a top, wherein the bottom of the sidewall has a first diameter, the canister has a circular open top portion disposed at the top of the sidewall, the circular open top portion has a second diameter that is greater than the first diameter, the canister has a domed bottom portion disposed at the bottom of the sidewall, and a smooth transition from the domed bottom portion to the bottom of the sidewall, the method comprising applying a vacuum to the interior of the canister to pull waste fluids into the canister during a medical procedure, wherein application of the vacuum causes the interior surface of the canister to be subject to only compressive stresses over a bottom half of the canister, thereby avoiding stress concentration distributions that cause cracks in the canister to close onto themselves.

* * * * *